US00PP09199P

United States Patent [19]

Asdoorian

[11] Patent Number: Plant 9,199

[45] Date of Patent: Jul. 18, 1995

[54] 'ISLAND KING' PEACH TREE

[76] Inventor: Alan R. Asdoorian, 522 6th Ave., Kingsburg, Calif. 93631

[21] Appl. No.: 261,400

[22] Filed: Jun. 16, 1994

[51] Int. Cl.[6] ..... A01H 5/00
[52] U.S. Cl. ..... Plt./43.1
[58] Field of Search ..... Plt. 43.1, 43.2

[56] References Cited

U.S. PATENT DOCUMENTS

P.P. 6,025 9/1987 Balakian ..... Plt./43.2

*Primary Examiner*—James R. Feyrer
*Attorney, Agent, or Firm*—Worrel & Worrel

[57] ABSTRACT

A new and distinct variety of peach tree which is somewhat similar to the "Queencrest" peach tree (U.S. Plant Pat. No. 6,025) from which it is a sport, but from which it is distinguished by producing an earlier ripening fruit which are mature for harvesting and shipment approximately two weeks prior to the fruit produced by the "Queencrest" peach tree.

1 Drawing Sheet

BACKGROUND OF THE NEW VARIETY

The present invention relates to a new and distinct variety of peach tree which will hereinafter be denominated varietally as the "Island King" peach tree and, more particularly, to a peach tree which produces clingstone fruit, which are mature for commercial harvesting and shipment approximately April 23 to April 25 in the San Joaquin Valley of central California as a very early, fresh market peach with a good red blush skin coloration.

In the development of new commercial varieties of fruit trees, a premium is frequently placed upon those varieties which produce fruit ripening early or late in the growing season when few competing varieties are available. However, typically such varieties are otherwise of marginal commercial appeal in that the fruit is of poor size, flavor, or coloration, or may suffer from any one or more other undesirable characteristics. These deficiencies are frequently more pronounced in the very earliest and very latest ripening varieties. Thus, in many instances a very early or very late ripening new variety, which otherwise would be a good candidate from commercial development, may be deemed unworthy because of one or more fatal flaws in these respects. The peach tree of the subject invention appears, conversely, to be a promising candidate in that while being a very early ripening variety, it does not appear to suffer from any such fatal flaws.

ORIGIN AND ASEXUAL REPRODUCTION OF THE NEW VARIETY

The present variety of peach tree was discovered by the inventor in his orchard of "Queencrest" peach trees (U.S. Plant Pat. No. 6,025) which is located near Kingsburg, Calif. in the San Joaquin Valley of central California. The inventor discovered the new variety as a sport of the "Queencrest" peach tree in 1992. The new variety was first asexually reproduced by the inventor in 1992 by bud grafting three trees in the orchard of origin to the new variety using buds from mature wood. The asexually reproduced trees first bore fruit of the new variety in April of 1993. The inventor carefully compared the asexually reproduced trees with the parent sport, including the fruit thereof, and has confirmed that the parent and its progeny are in all respects identical.

SUMMARY OF THE NEW VARIETY

The "Island King" peach tree is characterized by producing a clingstone fruit which has a good red blush coloration and is ripe for commercial harvesting and shipment approximately April 23 to April 25 in the San Joaquin Valley of central California. The new variety is most closely similar to the "Queencrest" peach tree (U.S. Plant Pat. No. 6,025) from which it is a sport, but from which it is distinguishable in that it ripens about ten days to two weeks earlier than the fruit of the "Queencrest" peach tree and in that the fruit is somewhat smaller in size than that of the "Queencrest" peach tree. The fruit of the instant variety possesses an acceptable flavor for such an early ripening variety.

BRIEF DESCRIPTION OF THE DRAWING

The accompanying drawing is a color photograph showing fruit of the new variety including a first in bottom plan view showing the apex end thereof; a second in side elevation showing the suture thereof; a third in side elevation showing the check surface thereof; a fourth in top plan view showing the stem cavity thereof; and a fifth sectioned to show the flesh thereof; and foliage typical of the new variety of peach tree.

DETAILED DESCRIPTION

Referring more specifically to the pomological details of this new and distinct variety of peach tree, the following has been observed under the ecological conditions prevailing at the orchard of origin which is located near Kingsburg, Calif. in the San Joaquin Valley of central California. All major color code designations are by reference to the *Dictionary of Color,* by Maerz and Paul, First Edition, 1930. Common color names are also occasionally employed.

TREE

Generally: Develops from 2.5 feet (75 cm) to 3.0 feet (90 cm) of new scaffold growth annually. This amount of top growth is about equivalent to that produced by the parent "Queencrest" peach tree.

*Vigor.*—Medium.

*Figure.*—The tree is upright to upright-spreading in form and has been developed by using the open vase system of training.

*Productivity.*—Productive.

*Regularity of bearing.*—Regular and hardy under typical central San Joaquin Valley climatic conditions.

Trunk:

*Size.*—Medium in thickness.

*Surface texture.*—Moderately rough.

*Color.*—Greyish-brown (15-A-6 Beaver).

*Lenticels — form.*—Oval and flattened longitudinally.

*Lenticels — size.*—Medium.

*Lenticels — length.*—Ranges from 4 mm (0.1575 inches) to 7 mm (0.2756 inches).

*Lenticels — height.*—Ranges from 1.5 mm (0.0591 inches) to 2.5 mm (0.0984 inches).

Branches:

*Size.*—Medium in thickness.

*Surface texture.*—Relatively smooth.

*Color — two years or older wood.*—Brownish-red (7-L-10 Kettledrum Brown).

*Color — immature branches.*—Pale green (17-J-6) often with reddish pigmentation on the side of the shoot exposed to direct sunlight.

*Internode — length.*—Upright shoots varies from 28 mm (1.102 inches) to 37 mm (1.457 inches).

*Tips — color.*—New shoot tips are shiny green-yellow (18-L-3).

LEAVES

Size:

*Generally.*—Medium to large in size. Leaf measurements have been taken from large leaves growing on vigorous upright current season's growth.

*Average length.*—Ranges from 13.7 cm (5.394 inches) to 15.3 cm (6.024 inches), including the petiole.

*Average width.*—Ranges from 3.0 cm (1.181 inches) to 3.5 cm (1.378 inches).

*Thickness.*—Average.

Form: Lanceolate. Leaf tip is acuminate.

Color:

*Upwardly disposed surface.*—Medium green (23-L-3 Hellebore Green).

*Downwardly disposed surface.*—Lighter grey-green (21-J-5 Asphodel Green).

Marginal form:

*Generally.*—Crenate with small regular crenations. The crenations are occasionally double near mid-margin.

Leaf margin: Slightly undulate.

Petiole:

*Size.*—Medium.

*Length.*—Ranges from 9 mm (0.3543 inches) to 11 mm (0.4331 inches).

*Thickness.*—Ranges from 1.5 mm (0.0591 inches) to 2.0 mm (0.0787 inches).

*Color.*—Green-yellow (19-K-5), darker green on the upper petiole surfaces and along the petiole groove (21-K-5 Biscay Green).

Glands:

*Size.*—Medium to large.

*Position.*—Alternate.

*Pattern.*—Most often, two large stalked reniform glands are present at the base of the leaf margin. From 0 to 4 additional smaller, mostly reniform glands can be present along the basal edges of the leaf margin.

*Form.*—Predominantly reniform, some form variability does exist with occasional globose gland types present.

Young glands:

*Color.*—Bright yellow-green (19-L-2 Javel Green), but the glands become darker and deteriorate with age.

Stipules:

*Size.*—Large.

*Length.*—Ranges from 13 mm (0.5118 inches) to 15.5 mm (0.6102 inches).

*Form.*—Linear lanceolate.

*Margins — form.*—Serrate and tipped with brownish colored trichomes.

*Color.*—Greenish-yellow (19-K-4) when young, turning reddish (4-J-11 Canna Red) with maturity and then becoming early deciduous.

FLOWERS

Flower buds: Hardy under typical central San Joaquin Valley climatic conditions.

*Size.*—Dormant floral buds are of average size.

*Form.*—Conic and very slightly appressed to the bearing branch.

Bud scales:

*Color.*—Medium brownish-grey (6-A-9 Manon Brown) and have a very pubescent surface.

Flowers:

*Generally.*—"Showy" type.

*Date of bloom.*—The bloom period of the new variety is early in relation to other common commerical peach varieties grown in the same region. In relation to the "Queencrest" peach tree the bloom is only very slightly later, about one day. Date of full bloom was in early March in 1993; that is, about five percent (5%) bloom was reached on Feb. 24, 1993 and full bloom on Mar. 9, 1993.

*Size — generally.*—Large.

*Diameter.*—Fully expanded ranges from 35 mm (1.378 inches) to 43 mm (1.693 inches).

*Bloom quantity.*—Abundant.

Petals:

*Size.*—Large.

*Length.*—Ranges from 18 mm (0.7087 inches) to 21 mm (0.8268 inches).

*Width.*—Ranges from 16 mm (0.6299 inches) to 20 mm (0.7874 inches).

*Form.*—Slightly variable, but is most frequently broadly ovate.

*Number.*—Five.

*Color.*—Generally new petals are a light pink (1-C-1), darker rose-pink (1-F-3) basally and on the petal claw. The petals usually become darker with age, especially basally.

Petal claw:

*Form.*—Broadly truncate.

*Width.*—Averages 1.5 mm (0.0591 inches).

*Length.*—Relatively short. Averages 1.5 mm (0.0591 inches).

Petal margins: Moderately to substantially undulate with a generally rounded to slightly domed apex.

Flower pedicel:

*Length.*—Short. Averages 2.0 mm (0.0787 inches).

*Thickness.*—Averages 1.5 mm (0.0591 inches).

*Color.*—Bright shiny green (19-L-6 Calliste Green).

*Surface.*—Glabrous.

Calyx:

*Color.*—Green (18-K-4) basally and maroon (7-H-4 Aubusson) near the base of the sepals.

*Surface.*—Glabrous.

Sepal:

*Surface.*—Pubescent.

*Size.*—Varies from medium to large.

*Form.*—Broadly ovate.

*Color.*—Maroon (7-H-4).

Nectaries:

*Color.*—Bright orange (9-G-12) when young, becoming slightly darker and duller with age.

Anthers:

*Size.*—Average.

*Color.*—Red (5-L-2) Chrysanthemum Red) dorsally and chamois (10-G-4) ventrally, often with red margins.

Pollen: Abundant.

*Color.*—Yellow-gold (10-L-4 Light Chrome).

Stamen:

*Length.*—Ranges from 12 mm (0.4724 inches) to 16 mm (0.6299 inches). The longest stamens are about equal to the length of the pistil.

Filament:

*Color.*—Very light pink (1-B-7 Pink #2) when young, darkening with age to a rose-pink (1-F-3).

Pistil:

*Length.*—Varies from 16 mm (0.6299 inches) to 18 mm (0.7087 inches), including the ovary.

*Color.*—Very pale green (18-D-2 Sea Foam Green) basally and pale yellow-green (18-F-1) along the style.

*Surface.*—Very pubescent.

FRUIT

Maturity when described: Ripe for commercial harvesting shipment approximately April 23 for first pick in 1993 and April 25 for last pick in 1993 near Kingsburg, Calif. in the San Joaquin Valley of central California.

Size:

*Generally.*—Uniform and small to medium in size.

*Average diameter in the axial plane.*—Ranges from 46 mm (1.811 inches) to 48 mm (1.890 inches).

*Average diameter in the suture plane.*—Ranges from 41 mm (1.614 inches) to 46 mm (1.811 inches).

*Average diameter cheek plane.*—Ranges from 42 mm (1.654 inches) to 46 mm (1.811 inches).

Form:

*Uniformity.*—Variable in lateral aspect from oval to slightly ovate. In apical aspect the fruit form ranges from globose to slightly oval.

*Symmetry.*—The fruit is usually asymmetrical with one side larger than the other.

Suture:

*Generally.*—A distinct suture line is present, running the full length of the fruit from apex to base. The suture is usually slightly deeper over the apical shoulder. Suture line is usually a stripe.

*Width.*—Ranges from 1.5 mm (0.0591 inches) to 2.0 mm (0.0787 inches).

*Color.*—Devoid of red coloration, taking on the yellow (17-I-1) to yellow-green (17-G-2) coloration of the underlying ground color.

Ventral surface:

*Generally.*—Usually uneven with moderate lipping. The lipping is usually stronger on one side of the fruit.

Stem cavity:

*Generally.*—Medium in size.

*Width.*—Varies from 15 mm (0.5916 inches) to 17 mm (0.6693 inches).

*Depth.*—Relatively shallow, ranging from 5 mm (0.1969 inches) to 7 mm (0.2756 inches).

*Length.*—Ranges from 15 mm (0.5916 inches) to 18 mm (0.7087 inches).

*Shape.*—Broadly oval to nearly globose in form.

Stem:

*Generally.*—Short.

*Length.*—Ranges from 4.5 mm (0.1772 inches) to 6.0 mm (0.2362 inches).

*Thickness.*—Varies from 2.5 mm (0.0984 inches) to 3.0 mm (0.1181 inches).

*Color.*—Green (20-L-3 Certosa Green) to brownish (15-H-7 Olive Brown).

Base:

*Shape.*—Variable, from rounded to slightly truncate. Base angle is usually very slightly oblique to the fruit axis.

Axis:

*Shape.*—Variable, from rounded to slightly pointed.

Pistil point: Oblique.

Skin:

*Thickness.*—Average with a pubescent surface. The pubescence is short, fine and greyish in color.

*Tenacity.*—The skin adheres tightly to the flesh at commercial maturity.

*Tendency to crack.*—No tendency for skin cracking was observed.

*Color — generally.*—Somewhat uneven. The amount of red blush coloration present ranges from 40 to 70 percent of the fruit surface. Blush form is mixed with both washed and striped areas present.

*Blush color.*—Varies from a dark garnet red (7-J-6 Garnet Red) at the apex to a lighter red-orange over the apical shoulders in both washed and striped patterns. Additionally, a lighter orange-red (4-I-11 Carnilian Red) coloration can be present randomly in uneven patterns over the fruit surface. A few light colored dots can be present, usually over the apical shoulders and near the apex.

*Ground color.*—Visible over 30 to 60 percent of fruit surface. Varies from a pale yellow (17-I-1) to a yellow-green (17-G-2).

*Flavor.*—Somewhat neutral with only slight acidity.

Flesh:

*Flesh color.*—Flesh coloration is uniform throughout the fruit. The flesh color is a light yellow (9-K-4 Jasmine Yellow). Numerous short, tender, light colored fibers are present throughout the flesh.

*Color of pit well.*—The color of the flesh at the stone cavity is essentially the same shade of yellow as the rest of the flesh.

*Level of sweetness.*—Tree ripe fruit is very sweet.

*Flavor.*—Mild with very slight astringency.

*Aroma.*—Very slight and pleasant.

*Texture.*—Firm and fine textured at commercial maturity.

*Ripening.*—Ripens first at the apex.

*Eating quality.*—Average for this very early season of maturity.

Stone:

*Attachment.*—Clingstone. The flesh is tightly attached to the stone at commercial maturity.

*Fibers — numbers.*—Numerous short fibers are attached to the stone surface throughout.

*Fibers — length.*—Short.

*Size.*—Small.

*Size — length.*—Ranges from 25 mm (0.9843 inches) to 28 mm (1.102 inches).

*Size — width.*—Ranges from 15 mm (0.5906 inches) to 19 mm (0.7480 inches).

*Size — thickness.*—Ranges from 12 mm (0.4724 inches) to 15 mm (0.5906 inches).

*Form — generally.*—Ovate, at times narrowly so. The stone is soft and relatively unlignified due to the very early season of maturity.

*Apex — shape.*—Acute with a sharp tip.

*Color — dry.*—Brownish-tan (13-C-8 Tuscan Tan).

*Base — shape.*—Slightly truncate. The base angle is most frequently oblique to the stone axis.

*Sides — generally.*—Usually unequal, but only slightly so.

*Hilum.*—hilum scar is very small, oval in form and substantially eroded.

*Surface.*—Grooved laterally, most heavily over the apical shoulder along the ventral suture and basally near the hilum. Pitting occurs most frequently laterally at mid-stone.

*Ventral edge.*—Relatively narrow. Several low coalesced wings are present, most prominent over the basal shoulder where a low keel is present.

*Ventral edge — width.*—Ranges from 2.5 mm (0.0984 inches) to 3.0 mm (0.1181 inches).

*Dorsal edge.*—Tight groove is present along the dorsal edge extending from base to apex. Low ridges are present on each side of the groove. The dorsal edge is slightly eroded over the apical shoulder.

*Tendency to split.*—A moderate number of split stones are present internally. Less splitting is in evidence externally.

Use: Fresh market.

Although the new variety of peach tree possesses the described characteristics noted above as a result of the growing conditions prevailing near Kingsburg, Calif. in the central San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of peach tree, what I claim as new and desire to be secured by plant letters patent is:

1. A new and distinct variety of peach tree substantially as illustrated and described which is somewhat remotely similar to the "Queencrest" peach tree (U.S. Plant Pat. No. 6,025) from which it is a sport, but from which it is distinguished by producing earlier maturing fruit with good exterior coloration and edible quality which are mature for commercial harvesting and shipment approximately April 23 to April 25, or about ten days to two weeks earlier than the fruit of the "Queencrest" peach tree.

* * * * *

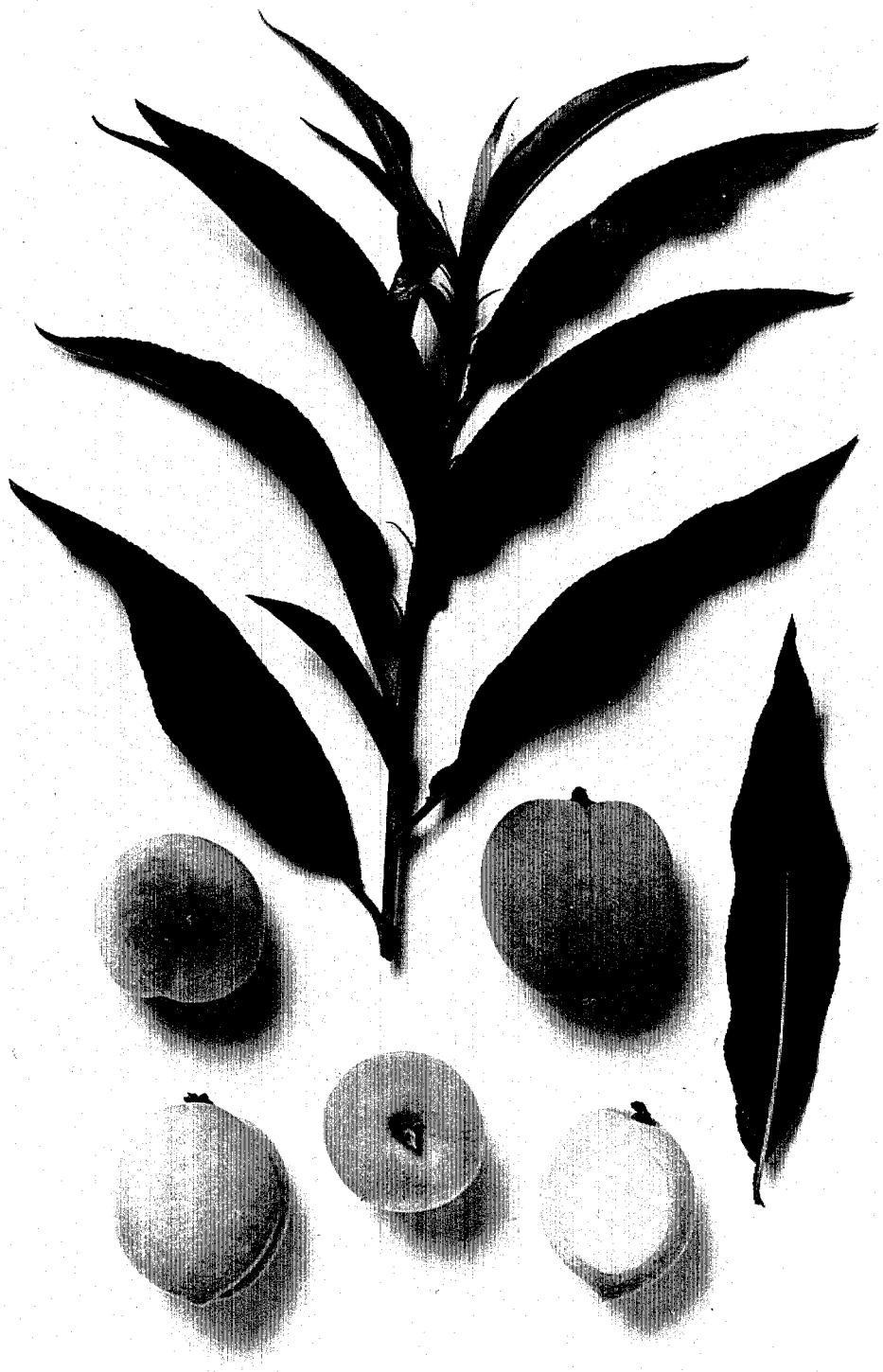

UNITED STATES PATENT AND TRADEMARK OFFICE

CERTIFICATE OF CORRECTION

PATENT NO. : PP 9,199

DATED : July 18, 1995

INVENTOR(S) : ALAN R. ASDOORIAN

It is certified that error appears in the above-identified patent and that said Letters Patent is hereby corrected as shown below:

Column 5, line 1, delete "7-H-4" and substitute
---7-H-5---;

Column 5, line 36, between "ing" and "shipment" add
---and---.

Signed and Sealed this

Tenth Day of October, 1995

*Attest:*

Bruce Lehman

BRUCE LEHMAN

*Attesting Officer*

*Commissioner of Patents and Trademarks*